United States Patent
Schmidt et al.

(10) Patent No.: US 12,054,843 B2
(45) Date of Patent: Aug. 6, 2024

(54) ACIDIC AQUEOUS COMPOSITION FOR ELECTROLYTICALLY DEPOSITING A COPPER DEPOSIT

(71) Applicant: Atotech Deutschland Gmbh & Co. KG, Berlin (DE)

(72) Inventors: Ralf Schmidt, Berlin (DE); Josef Gaida, Berlin (DE); Willi Rohland, Berlin (DE); Jens Palm, Berlin (DE); Himendra Jha, Berlin (DE)

(73) Assignee: Atotech Deutschland Gmbh & Co. KG, Berlin (DE)

( * ) Notice: Subject to any disclaimer, the term of this patent is extended or adjusted under 35 U.S.C. 154(b) by 0 days.

(21) Appl. No.: 17/920,509

(22) PCT Filed: Apr. 22, 2021

(86) PCT No.: PCT/EP2021/060592
§ 371 (c)(1),
(2) Date: Oct. 21, 2022

(87) PCT Pub. No.: WO2021/214255
PCT Pub. Date: Oct. 28, 2021

(65) Prior Publication Data
US 2023/0142446 A1     May 11, 2023

(30) Foreign Application Priority Data
Apr. 23, 2020 (EP) .................................... 20171018

(51) Int. Cl.
*C25D 5/16*     (2006.01)
*C07D 233/60*     (2006.01)
(Continued)

(52) U.S. Cl.
CPC ............. *C25D 3/38* (2013.01); *C07D 233/60* (2013.01); *C07D 249/04* (2013.01); *C07D 251/54* (2013.01)

(58) Field of Classification Search
None
See application file for complete search history.

(56) References Cited

U.S. PATENT DOCUMENTS

| 3,399,151 A | 8/1968 | Kaiser |
| 4,009,087 A | 2/1977 | Kardos et al. |

(Continued)

FOREIGN PATENT DOCUMENTS

| DE | 4225961 C2 | 2/1994 |
| JP | 2013023693 A | 2/2013 |

(Continued)

OTHER PUBLICATIONS

PCT/EP2021/060592; International Search Report and Written Opinion of the International Searching Authority dated Jul. 14, 2021.
(Continued)

*Primary Examiner* — Wojciech Haske
(74) *Attorney, Agent, or Firm* — Renner, Otto, Boisselle & Sklar, LLP

(57) ABSTRACT

The invention relates to an acidic aqueous composition for electrolytic copper plating, the composition comprising
(i) copper (II) ions,
(ii) one or more than one suppressor consisting of or comprising
one single N-heteroaromatic mono-ring, said mono-ring comprising at least two ring nitrogen atoms and more than one substituent covalently connected to one of said ring nitrogen atoms and/or a ring carbon atom, wherein said substituent independently is or comprises
one or more than one linear or branched polyalkylene glycol moiety, and/or
(Continued)

one or more than one linear or branched polyalkylene glycol block polyalkylene glycol, or random polyalkylene glycol moiety, with the proviso that if said suppressor comprises a OH group, then it is a terminal OH group of said polyalkylene glycol moiety, polyalkylene glycol block polyalkylene glycol, and random polyalkylene glycol moiety, respectively, and said suppressor does not comprise $NH_2$ groups, halogen atoms, and sulfur atoms;

a method of electrolytic copper plating using the acidic aqueous composition; and specific suppressors as defined above.

9 Claims, 1 Drawing Sheet

(51) Int. Cl.
| | | |
|---|---|---|
| *C07D 249/04* | (2006.01) | |
| *C07D 251/54* | (2006.01) | |
| *C25D 3/38* | (2006.01) | |
| *C25D 5/00* | (2006.01) | |
| *C25D 5/12* | (2006.01) | |
| *C25D 5/50* | (2006.01) | |

(56) References Cited

U.S. PATENT DOCUMENTS

| | | |
|---|---|---|
| 4,385,967 A | 5/1983 | Brady et al. |
| 4,496,436 A | 1/1985 | Inoue |
| 4,776,939 A | 10/1988 | Blasing et al. |
| 5,976,341 A | 11/1999 | Schumacher et al. |
| 6,099,711 A | 8/2000 | Dahms et al. |
| 8,679,316 B2 | 3/2014 | Brunner et al. |
| 9,506,158 B2 | 11/2016 | Rohde et al. |
| 9,551,080 B2 | 1/2017 | Brunner et al. |
| 9,598,787 B2 | 3/2017 | Jayaraju et al. |
| 11,035,051 B2 | 6/2021 | Si et al. |
| 2001/0026890 A1 | 10/2001 | Ono et al. |
| 2005/0247577 A1 | 11/2005 | Pavlov et al. |
| 2016/0143152 A1* | 5/2016 | Kozhukh ............... C25D 3/32 205/297 |

FOREIGN PATENT DOCUMENTS

| | | |
|---|---|---|
| JP | 2017066448 A | 4/2017 |
| WO | 2008157612 A1 | 12/2008 |
| WO | 2016169952 A1 | 10/2016 |

OTHER PUBLICATIONS

Jadhav Vinod H et al.; "Organocatalysis of nucleophilic substitution reactions by the combined effects of two promoters fused in a molecule: oligoethylene glycol substituted imidazolium salts", Tetrahedron, Elsevier Sience Publishers, Amsterdam, NL, vol. 70, No. 2, Jan. 14, 2014, pp. 533-542, XP028803845.

Anders Riisager et al.; "Thermomorphic phase separation in ionic liquid organic liquid systems-conductivity and spectroscopic characterization", Physical Chemistry Chemical Physics, vol. 7, No. 16, Jan. 1, 2005, p. 3052, XP055737055.

L. Corda et al.; "Electron Impact and Fast Atom Bombardment Mass Spectrometry in the Characterization of Some New Macrocycles Containing a 1,3,5-Triazine Moiety", Organic Mass Spectrometry, vol. 27, Jan. 1, 1992, pp. 1194-1198, XP055737115.

\* cited by examiner

ACIDIC AQUEOUS COMPOSITION FOR ELECTROLYTICALLY DEPOSITING A COPPER DEPOSIT

This application is a national phase of International Application No. PCT/EP2021/060592, filed 22 Apr. 2021, which claims priority to European Patent Application No. 20171018.3, filed 23 Apr. 2020, each of which is hereby incorporated herein by reference in its entirety.

FIELD OF THE INVENTION

The present invention relates to an acidic aqueous composition (plating bath) for electrolytic copper plating (electrolytic deposition of copper), the composition comprising copper (II) ions, one or more than one suppressor with the definitions given below, a method of electrolytic copper plating using the acidic aqueous composition according to the invention, and specific suppressors as defined above for electrolytically depositing a copper deposit.

The acidic aqueous composition according to the present invention is suitable in the electrolytic deposition of copper, in particular for filling blind micro vias (BMVs), through vias, trenches and similar structures. Thus, the method of the present invention is suitable in the manufacture of printed circuit boards (PCB), integrated circuit (IC) substrates and the like as well as for metallization of semiconducting and glass substrates.

BACKGROUND OF THE INVENTION

Acidic aqueous compositions (aqueous acidic plating baths) for electrolytic copper plating (electrolytic deposition of copper) are used for manufacturing printed circuit boards (PCB) and IC substrates where fine structures like trenches, through holes (TH), blind micro vias (BMV), pillar, and bumps need to be filled or build up with copper. Another application of such compositions is filling of recessed structures such as through silicon vias (TSV) and dual damascene (DD) structures or feature, plating or forming redistribution layers (RDL) and pillar bumps.

With the progressive miniaturization of printed circuit boards, design and complexity are constantly increasing. It is typically the aim to increase the calculating capacity and/or functionality in an ever-decreasing space. Along with it, the geometry, for example of the printed circuit boards or of the conductor structures on printed circuit boards, chip carriers and semiconductor wafers is becoming more and more complex and complicated. For example, the ratio of the copper thickness to the width of a conductor path or respectively of the hole depth relative to the diameter of the hole (aspect ratio) is constantly becoming greater as the hole diameters are becoming smaller and smaller and the conductor paths narrower and narrower.

It is generally accepted that structures exhibiting a comparatively high aspect ratio (e.g. 6:1 to 3:1) demand a sophisticated method of electrolytic copper plating because such structures exhibit a variable electric depositing behavior. In particular, it has been shown in our own experiments that the formation of uniform and reliable conductor structures in trenches and vias on printed circuit boards, using methods known in the art, is in many cases insufficient and often very difficult. For example, due to the comparatively increased aspect ratio of structures (and, thus, the variable electric depositing behavior), a copper layer with an uneven surface is often formed as the copper is being deposited. An uneven surface, however, often results in additional challenges during chemical/mechanical polishing after the deposition of copper. It is typically a prerequisite for respective polishing steps that the copper surfaces generated during the electrolytic deposition process are extensively smooth and even so that metal can be removed in a reliable manner up to the desired depth. Furthermore, a smooth and even surface contributes to a high level of reproducibility.

Adding numerous different organic additives to aqueous compositions for electrolytic copper plating in order to enable the decorative and functional characteristics of the copper coatings to be controlled is well known.

A so-called "suppressor" can be used, which "is typically a polymeric organic species, e.g., high molecular weight polyethylene or polypropylene glycol, which adsorbs strongly on the copper cathode surface to form a film that sharply increases the overpotential for copper deposition. This prevents uncontrolled copper plating [ . . . ]" (see US 2005/0247577 A1, paragraph [0007]). Further an anti-suppressor (also known as "accelerator") can be used, having the purpose "to counter the suppressive effect of the suppressor and provide the accelerated deposition within substrate recesses needed for leveling" (see again US 2005/0247577 A1, paragraph [0007]).

In order to obtain properly copper filled structures, further an organic additive can be typically used, as "leveller". A "leveller" "is typically an organic compound containing nitrogen that tends to decrease the copper plating rate" (see US 2005/0247577 A1, paragraph [0009]).

JP 2013 023693 A discloses a copper plating bath comprising an imidazole ring-bonded oxyalkylene compounds with the ring at the end. The compound is considered to provide good solubility in water and high defoaming property in the plating bath.

The above-mentioned additives often positively affect the uniform deposition and metallization of copper during the plating process. It has been shown that in very small structures that are to be completely filled by copper such additives usually help avoiding the formation of hollow spaces (voids) in the copper deposit.

Unfortunately, in some cases organic additives are co-deposited along with metal ions (e.g. copper ions) assuming that undesired effects such as increased electromigration and reliability issues result. It is generally assumed that the co-deposition of such additives is increased if the adhesion of said additives towards the plating surface is very strong. Thus, there is a demand for additives exhibiting proper adhesion properties.

Furthermore, it is basically assumed that the copper filling quality of structures exhibiting a comparatively high aspect ratio (e.g. 6:1 to 3:1) correlates with the overpotential generated in a respective acidic aqueous composition for electrolytic copper plating (J. Electrochem. Soc. 2004, 151, C702-C711).

There is an ongoing demand to provide new and improved acidic aqueous compositions for electrolytic copper plating (and respective plating methods) in order to obtain uniform and void-free copper deposits, wherein the deposits contain comparatively low amounts of organic additives. Furthermore, respective compositions should exhibit an adequate stability (shelf life).

EP 2 778 260 A2 discloses methods of filling through-holes. The disclosed methods inhibit or reduce dimpling and voids during copper electroplating of through holes with flash copper layers in substrates such as printed circuit boards. EP 2 778 260 A2 discloses an aqueous acid solution consisting essentially of one or more inorganic acids and one or more reaction products of one or more aromatic heterocyclic nitrogen compounds and one or more epoxy-containing compounds, the one or more reaction products are in amounts of 1 ppm to 50 ppm.

U.S. Pat. No. 4,009,087 A relates to a process and to novel compositions for electrodepositing copper from an aqueous acidic copper plating bath. The bath contains at least one member independently selected from each of the two groups (i) an N-heteroaromatic compound containing 1 or 2 N-heteroaromatic rings and sulfoalkylsulfide and sulfoarylsulfide compounds.

OBJECTIVE OF THE PRESENT INVENTION

It is the objective of the present invention to provide an acidic aqueous composition (plating bath) for electrolytic copper plating (electrolytic deposition of copper) exhibiting good plating qualities (i.e. basically free of voids and obtaining a uniform deposition of copper) during the electrolytic plating process, in particular for a substrate with structures exhibiting both low and high aspect ratios.

It was an additional objective to provide an acidic aqueous composition that exhibits an increased overpotential compared to a composition comprising typically polyethylene glycol (PEG) as suppressor additive.

It is furthermore desired that such compositions exhibit an adequate stability (shelf life) and lead to copper deposits containing comparatively low amounts of organic additives, i.e. exhibit an adequate adhesion on the copper surface.

It is furthermore an objective of the present invention to provide a respective method for electrolytic copper plating (electrolytic deposition of copper), which allows a comparatively fast copper filling of structures exhibiting low and high aspect ratios on the one hand and an adequate plating quality (e.g. good surface distribution over the whole substrate and less co-deposition of organic additives) on the other hand.

SUMMARY OF THE INVENTION

The objectives mentioned above are solved by an acidic aqueous composition for electrolytic copper plating and the suppressor for electrolytically depositing a copper deposit as described in the following, the composition comprising
  (i) copper (II) ions,
  (ii) one or more than one suppressor consisting of or comprising
    one single N-heteroaromatic mono-ring, said mono-ring comprising at least two ring nitrogen atoms and more than one substituent covalently connected to one of said ring nitrogen atoms and/or a ring carbon atom, wherein said substituent independently is or comprises
    one or more than one linear or branched polyalkylene glycol moiety, and/or
    one or more than one linear or branched polyalkylene glycol block polyalkylene glycol or random polyalkylene glycol moiety,
    with the proviso that
    if said suppressor comprises a OH group, then it is a terminal OH group of said polyalkylene glycol moiety, polyalkylene glycol block polyalkylene glycol or random polyalkylene glycol moiety, respectively, and
    said suppressor does not comprise $NH_2$ groups, halogen atoms, and sulfur atoms.

Throughout the text said suppressor as described above and used as compound (ii) in the acidic aqueous composition for electrolytic copper plating is named "suppressor (ii)". Preferred embodiments of said suppressor (ii) are defined below.

The suppressor preferably does not comprise a group which is covalently connected to one of said ring nitrogen atoms and/or a ring carbon atom, which is usable for polymerisation as a group having a double or threefold bond between two carbon atoms, e.g. an alkenyl group or an alkynyl group.

Throughout the text the term "said suppressor does not comprise $NH_2$ groups, halogen atoms, and sulfur atoms" means that the suppressor does not contain covalent bonded $NH_2$ groups, halogen atoms, and sulfur atoms within the organic structure of the suppressor. In contrast, if the suppressor comprises positive charged parts (atoms) within the organic structure as a positive charged nitrogen atom (shown as $N^+$) then the negative charged counter group is a negative charged ionic counter group and can be a halide as a chloride or a sulphur-containing group as a sulphate. The bonding between the positive charged parts within the organic structure and the negative charged ionic counter group is an ionic bonding (and not a covalent bonding), wherein the e.g. positive charged nitrogen atom remains covalent bonded to its adjacent atoms within the organic structure of the suppressor. The negative charged counter group does not affect the activity of the suppressor as such and can dissociate in the acidic aqueous composition for electrolytic copper plating.

In case the suppressor comprises a positive charged parts (atoms) within the organic structure of the suppressor, the suppressor comprises also a negative charged counter group $X^-$. Preferably the negative charged counter group is a negative charged ionic counter group selected from the group consisting of a sulphur-containing group as sulphate. More preferably the suppressor also does not comprise halides as negative charged counter group.

Throughout the text the term "more than one" is understood as two or more, three or more, four or more and so on.

Furthermore, the objectives are solved by a method of electrolytic copper plating, comprising the steps
  (a) providing or manufacturing a substrate suitable for electrolytic copper plating,
  (b) contacting the substrate obtained after step (a), or obtained after an additional step after step (a) but before step (b), with the acidic aqueous composition according to the present invention (as defined above, preferably as defined below as being preferred) and applying an electrical current such that copper is electrolytically plated onto the substrate as a copper deposit.

DETAILED DESCRIPTION OF THE INVENTION

Figure 1:
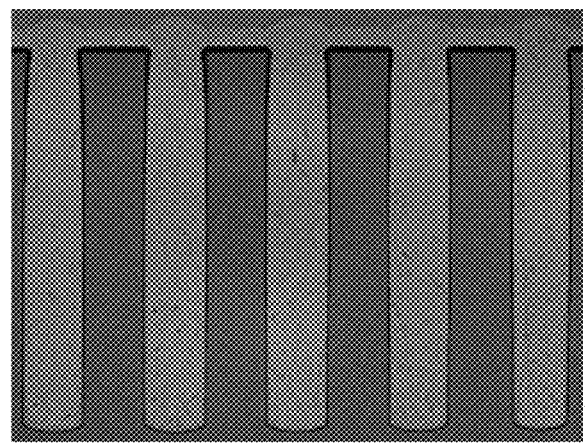
FIG. 1 is a photograph of a cross section of the copper metallized wafer substrate obtained by Example 1 as an embodiment of the present invention.

According to our own experiments (see section "Examples" below in the text), the acidic aqueous composition according to the present invention typically provided very good copper fillings (free of voids) for structures exhibiting low and high aspect ratios (see "Examples"). Furthermore, it was possible to obtain very good surface distribution of the copper deposition over the whole substrate. With other words, the copper thickness is very equal on every position on the substrate (both for pattern plating and panel plating).

Our own experiments have also shown that the acidic aqueous composition according to the present invention (as defined above) exhibits a significantly increased overpotential, compared to an acidic aqueous composition (not according to the invention) comprising polyethylene glycol instead of a compound of component (ii).

The acidic aqueous composition according to the present invention (as defined above) is an aqueous solution. The term "aqueous solution" means that the prevailing liquid medium, which is the solvent in the composition, is water. In some cases, it is preferred that the composition comprises liquids that are miscible with water. Preferred liquids are alcohols that are miscible with water. For ecological reasons, water as the sole solvent is preferred.

The acidic aqueous composition according to the invention (as defined above, preferably defined as being preferred) is typically prepared by dissolving all components and compounds (and subsequent stirring), respectively, in the aqueous liquid medium, preferably in water.

The composition according to the present invention (as defined above, preferably defined as being preferred) contains one or more than one acid, preferably selected from the group consisting of sulphuric acid, fluoroboric acid, phosphoric acid and methane sulphonic acid. The total amount of the one or more than one acid in the composition according to the present invention is preferably in a range of from 5 g/L to 400 g/L, more preferably in a range of from 10 g/L to 300 g/L, based on the total volume of the composition. If the total amount is much above 400 g/L the effect is that the bottom-up fill in the trench may be insufficient. These acids are preferably counted among the one, two, three or more than three further compounds.

The pH value of the composition according to the present invention (as defined above, preferably defined as being preferred) is 3 or less, preferably 2 or less, measured at a temperature of 20° C. This means that the pH value of the composition of the present invention is 3 or less, preferably 2 or less. In the context of the present invention the pH value is determined at a temperature of 20° C., i.e. the defined pH value is referenced to 20° C. Thus, only for the sake of pH determination the composition has a temperature of 20° C. This does not mean that the composition of the present invention in itself is limited to the specific temperature of 20° C. For preferred temperatures of the composition see below.

If the pH is much above 3 the effect is that the conductivity in the composition is mostly insufficient leading to an unbalanced current density in the composition while plating. Furthermore, a pH of 3 or below prevents the formation of insoluble copper oxide. As a result, no complexing agents are needed in the composition of the present invention. Thus, preferred is an acidic aqueous composition for electrolytic copper plating according to the present invention being substantially free of (preferably does not contain) complexing agents. The absence of complexing agents is preferred because the risk to include organic additives into the copper deposit is further minimized. If no complexing agents are included in the composition of the present invention typically no significant carbon content is observed in the copper deposit. Preferably, the electrolytically plated copper obtained in the method of the present invention comprises at least 99 weight-% copper, based on the total weight of the electrolytically plated copper, more preferably at least 99.9 weight-% copper.

The acidic aqueous composition for electrolytic copper plating according to the present invention comprises copper (II) ions. Preferably, the copper ion source is selected from the group consisting of copper sulphate, copper chloride, copper nitrate, copper fluoroborate, copper acetate, copper citrate, copper phenyl sulphonate, copper para-toluene sulphonate, and copper alkyl sulphonates. A preferred copper alkyl sulphonate is copper methane sulphonate. The most preferred copper source is copper sulphate, most preferably $CuSO_4 \cdot 5 H_2O$.

Preferably, the total amount of copper sulphate ($CuSO_4 \cdot 5 H_2O$) in the acidic aqueous composition for electrolytic copper plating according to the present invention is 12 g/L to 275 g/L, preferably 20 g/L to 275 g/L, based on the total volume of the acidic aqueous composition. In some specific cases a total amount of 30 g/L to 80 g/L is preferred, wherein in other specific cases a total amount of 180 g/L to 220 g/L is preferred. Respective molar amounts per litre can be calculated by the skilled person for the total amount of copper (II) ions if sources other than $CuSO_4 \cdot 5 H_2O$ are used. In some cases, a total amount of copper (II) ions (irrespective of the copper source) is preferred corresponding to the aforementioned concentrations for copper sulphate ($CuSO_4 \cdot 5 H_2O$) in g/L.

In general, in the composition according to the invention (as defined above, preferably defined as being preferred) the total amount of copper (II) ions is in the range of from 3 to 70 g/L, preferably in the range of from 5 to 70 g/L, based on the total volume of the composition.

Preferred is a composition of the present invention, wherein said copper (II) ions in the composition represent at least 95 mol-% of all depositable metal cations in the composition, more preferably at least 98 mol-%, even more preferably at least 99 mol-%, most preferably 99.9 mol-%.

"Depositable metal cations" are cations that are deposited in metallic form together with copper if an electric current is applied. Such a "depositable metal cation" is for example tin, nickel and silver.

Preferred is a composition of the present invention, wherein said copper (II) ions in the composition represent at least 95 mol-% of all transition metal cations in the composition, more preferably at least 98 mol-%, even more preferably at least 99 mol-%, most preferably at least 99.9 mol-%. More preferred is a composition of the present invention, wherein said copper (II) ions in the composition represent at least 95 mol-% of all transition metal cations together with metal ions of main groups III, IV, and V of the periodic table, more preferably at least 98 mol-%, even more preferably at least 99 mol-%, most preferably at least 99.9 mol-%.

Preferably, the acidic aqueous composition of the present invention is not for a copper alloy.

Most preferred is a composition of the present invention, wherein said copper (II) ions are the only depositable metal cations. Thus, the electrolytically plated copper in the method of the present invention is most preferably pure copper. In the context of the present invention, "pure copper" denotes that the electrolytically plated copper comprises at least 99.5 weight-% copper, based on the total weight of the electrolytically plated copper.

Preferred is a composition of the present invention, wherein the composition is substantially free of (preferably does not contain) transition metals other than copper. Also preferred is a composition, wherein the composition is (preferably in addition to the aforementioned) substantially free of (preferably does not contain) aluminium, gallium, indium, tin, and lead.

In the context of the present invention, the term "substantially free" of a subject-matter (e.g. a compound, a metal ion, etc.) denotes that said subject-matter is not present at all or is present only in (to) a very little and undisturbing amount (extent) without affecting the intended purpose of the invention. For example, such a subject-matter might be added or utilized unintentionally, e.g. as unavoidable impurity. "Substantially free" preferably denotes 0 (zero) ppm to 50 ppm, based on the total weight of the composition of the present invention, if defined for said composition, or based on the total weight of the electrolytically plated copper obtained in the method of the present invention, if defined for said plated copper; preferably 0 ppm to 25 ppm, more preferably 0 ppm to 10 ppm, even more preferably 0 ppm to 5 ppm, most preferably 0 ppm to 1 ppm.

The acidic aqueous composition for electrolytic copper plating according to the present invention (as defined above, preferably defined as being preferred) comprises one or more than one suppressor (ii) (as defined above and below, preferably at least one or more than one suppressor (ii) defined as being preferred). In some cases it is preferred that the acidic aqueous composition for electrolytic copper plating according to the present invention (as described above, preferably defined as being preferred) comprises only one suppressor (ii) (as defined above and below, preferably one suppressor (ii) defined as being preferred). Without to be bound by theory it is assumed that the inventive suppressor (ii) combines positive features of different known suppressors and levellers. By using the inventive suppressor (ii) an additional suppressor (iii) and/or leveller is not needed or at least the concentration of the additional suppressor and/or leveller can be very low.

Throughout the text the word "independently" (e.g. in terms such as "independently selected" or "independently denote(s)") is used for moieties and groups. The meaning of this word is explained by means of the following example: For an example-compound X with example-groups E, F, and G, "E, F, and G are independently selected from a group consisting of [ . . . ]". This means that (i) example-group F in example-compound X is independently selected from example-groups E and G in the example-compound X and (ii) example-group F in example-compound X is independently selected from other example-groups F in other example-compounds, e.g. in an example-compound Y.

Throughout the text the term "alkyl" is used and refers to a univalent group derived from alkanes by removal of a hydrogen atom from any carbon atom ($C_nH_{2n+1}$). The term e.g. "C3 to C16 alkyl" refers to an alkyl group with 3 to 16 carbon atoms (n=3 to 16). Throughout the text C3 alkyl explicitly includes n-propyl and iso-propyl, C4 alkyl explicitly includes n-butyl, iso-butyl, sec-butyl, tert-butyl and C5 alkyl explicitly includes

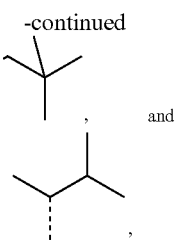

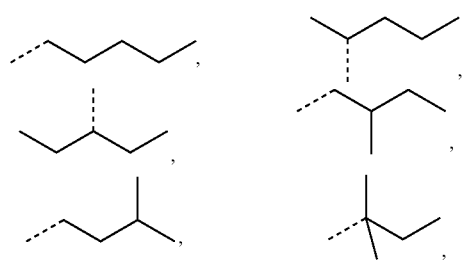

wherein the dashed line represents the covalent bond for binding the respective carbon atom of the alkyl radical with the respective atom of a molecule (connecting bond).

Throughout the text the term "polypropylene" is used and refers to polypropylene which can be based on n-propyl units or iso-propyl units.

Preferably, in the acidic aqueous composition for electrolytic copper plating according to the invention (as defined above, preferably defined as being preferred) the total amount of component (ii) (the total amount of the one suppressor (ii) or the total amount of all suppressors (ii) if more than one suppressor (ii) is present) is at least 10 mg/L, preferably at least 50 mg/L, more preferably at least 70 mg/L, and even more preferably at least 80 mg/L, based on the total volume of the acidic aqueous composition. Preferably, the total amount is not exceeding 1 g/L, based on the total volume of the acidic aqueous composition, preferably not exceeding 700 mg/L, more preferably not exceeding 500 mg/L. An acidic aqueous composition for electrolytic copper plating according to the invention is preferred, wherein the one or more than one suppressor (ii) is present in a total amount in the range from 10 mg/L to 1000 mg/L, based on the total volume of the acidic aqueous composition, preferably in the range from 50 mg/L to 700 mg/L, more preferably in the range from 70 mg/L to 500 mg/L, most preferably in the range from 80 mg/L to 400 mg/L.

Preferably, in the acidic aqueous composition for electrolytic copper plating according to the invention (as defined above, preferably defined as being preferred) comprises
 (iii) at least one additional suppressor being different from the suppressor (ii) and/or
 (iv) at least one accelerator being different from the suppressor(s) (ii) and (iii).

Preferably, the acidic aqueous composition for electrolytic copper plating according to the present invention (as defined above, preferably defined as being preferred) comprises one, two, three or more than three further compounds, which are different from the suppressor(s) (ii), the additional suppressor (iii) or the accelerator (iv). Preferably, the one, two, three or more than three further compounds are selected from the group consisting of one or more than one species of inorganic ions, one or more than one leveller compound, and one or more than one wetting agent.

Preferably, the composition of the present invention is substantially free of, preferably does not comprise, complexing agents.

A preferred species of inorganic ions is selected from the group consisting of halide ions (preferably chloride ions) and sulphate ions. They may be fully or partly added to the acidic aqueous composition according to the present invention by means of the copper source (for various copper sources see the text above). Other suitable sources for halide ions are for example hydrochloric acid or alkali halides such as sodium chloride.

Preferred is a composition of the present invention, wherein the one, two, three or more than three further compounds comprise halide ions, preferably chloride ions.

Preferably, in the acidic aqueous composition for electrolytic copper plating according to the present invention (as defined above, preferably defined as being preferred) the total amount of chloride ions is in the range of from 0.01 to 0.18 g/L, preferably in the range of from 0.03 to 0.10 g/L, based on the total volume of the acidic aqueous composition. Preferably, the total amount of hydrochloric acid is in the range of from 0.01 to 0.18 g/L, preferably in the range of from 0.03 to 0.10 g/L, based on the total volume of the acidic aqueous composition.

In a preferred embodiment of the invention, the suppressor (II) does not comprise halides as negative charged counter group in order not to add additional halide ions in particular chloride ions to the acidic aqueous composition for electrolytic copper plating.

The acidic aqueous composition for electrolytic copper plating according to the present invention (as defined above, preferably defined as being preferred) preferably contains sulfuric acid. Preferably, the total amount of sulfuric acid added in order to prepare a composition according to the present invention is in the range of from 5 g/L to 350 g/L, preferably in the range of from 5 g/L to 220 g/L, based on the total volume of the acidic aqueous composition. More preferred is a total amount in the range of from 5 g/L to 140 g/L or 180 g/L to 220 g/L. The sulfuric acid can also be replaced partially or completely by fluoroboric acid, methane sulfonic acid or other acids.

In some cases, it is preferred that the acidic aqueous composition according to the present invention comprises a redox couple, more preferably Fe (II)/Fe (III) ions. Such a redox couple is particularly useful, if reverse pulse plating is used in combination with inert anodes for copper deposition. Suitable processes for copper plating using a redox couple in combination with reverse pulse plating and inert anodes are for example disclosed in U.S. Pat. Nos. 5,976,341 and 6,099,711.

The at least one accelerator (iv) is preferably selected from the group consisting of thiol-, sulphide-, disulphide- and polysulphide-compounds. More preferred accelerators are selected from the group consisting of 3-(benzthiazolyl-2-thio)-propylsulphonic-acid, 3-mercaptopropan-1-sulphonic acid, ethylendithiodipropylsulphonic-acid, bis-(p-sulphophenyl)-disulphide, bis-(ω-sulphobutyl)-disulphide, bis-(ω-sulphohydroxypropyl)-disulphide, bis-(sodiumsulfopropyl)disulphide, bis-(ω-sulphopropyl)-disulphide, bis-(ω-sulphopropyl)-sulphide, methyl-(ω-sulphopropyl)-disulphide, methyl-(ω-sulfopropyl)-trisulphide, O-ethyl-dithiocarbonic-acid-S-(ω-sulphopropyl)-ester, thioglycolic acid, thiophosphoric-acid-O-ethyl-bis-(ω-sulphopropyl)-ester, 3-N,N-dimethylaminodithio-carbamoyl-1-propanesulphonic acid, 3,3'-thiobis(1-propanesulphonic acid), thiophosphoric-acid-tris-(ω-sulphopropyl)-ester and their corresponding salts. The total amount of accelerators is preferably in the range of from 0.001 g/L to 0.5 g/L, more preferably in the range from 0.005 g/L to 0.2 g/L, even more preferably in the range of from 0.01 g/L to 0.100 g/L, based on the total volume of the acidic aqueous composition.

The at least one additional suppressors (iii) is preferably selected from the group consisting of polyvinyl alcohol, carboxymethylcellulose, polyethylene glycol, polypropylene glycol, stearic acid polyglycolester, alkoxylated naphtoles, oleic acid polyglycolester, stearylalcoholpolyglycolether, nonylphenolpolyglycolether, octanolpolyalkylenglycolether, octanediol-bis-(polyalkylenglycolether), poly(ethylenglycol-ran-propylenglycol), poly(ethylenglycol)-block-poly(propyleneglycol)-block-poly(ethylenglycol), and poly(propylenglycol)-block-poly(ethylenglycol)-block-poly(propylenglycol). More preferably, the additional suppressor is selected from the group consisting of polyethylene glycol, polypropylene glycol, poly(ethylene glycol-ran-propylene glycol), poly(ethylenglycol)-block-poly(propyleneglycol)-block-poly(ethylenglycol), and poly(propylenglycol)-block-poly(ethylenglycol)-block-poly(propylenglycol). The total amount of additional suppressor compounds is preferably in the range of from 0.005 g/L to 20 g/L, more preferably in the range of from 0.01 g/L to 5 g/L.

Own reference experiments have shown that acidic aqueous reference compositions (not according to the present invention; i.e. without a suppressor (ii) but comprising additional suppressors (iii) (e.g. as defined above) also often result in a smoother, more homogeneous copper surfaces, compared to a copper surface obtained in the absence of such an additional suppressor (iii). Furthermore, also many of the aforementioned compounds typically contribute to an adequate overpotential in the respective reference compositions. However, the overpotential obtained in such a reference composition is usually considerably lower compared to an acidic aqueous composition according to the present invention.

Thus, in some cases it is preferred that the acidic aqueous composition according to the present invention is substantially free of, preferably does not contain one or more than one additional suppressor (iii) selected from the group consisting of polyvinyl alcohol, carboxymethylcellulose, polyethylene glycol, polypropylene glycol, stearic acid polyglycolester, alkoxylated naphtoles, oleic acid polyglycolester, stearylalcoholpolyglycolether, nonylphenolpolyglycolether, octanol-polyalkylenglycolether, octanediol-bis-(polyalkylenglycolether), poly(ethylenglycol-ran-propylenglycol), poly(ethylenglycol)-block-poly(propyleneglycol)-block-poly(ethylenglycol), and poly(propylenglycol)-block-poly(ethylenglycol)-block-poly(propylenglycol). However, in other cases it appears acceptable to additionally include one or more than one additional suppressor as defined above. In many cases, our own experiments have shown that the comparatively high overpotential generated in the acidic aqueous compositions according to the present invention is not negatively affected in the presence of additional suppressor as defined above.

Additionally, in some cases, at least one leveller compounds can be used. Preferred leveller are selected from the group consisting of nitrogen containing leveller compounds such as polyethyleneimine, alkoxylated polyethyleneimine, alkoxylated lactames and polymers thereof, diethylenetriamine and hexamethylenetetramine, dyes such as Janus Green B, Bismarck Brown Y and Acid Violet 7, sulphur containing amino acids such as cysteine, and phenazinium salts. Further nitrogen containing levellers can be polyethylenimine bearing peptides, polyethylenimine bearing amino acids, polyvinylalcohol bearing peptides, polyvinylalcohol bearing amino acids, polyalkylenglycol bearing peptides, polyalkylenglycol bearing amino acids, aminoalkylen bearing pyrrols and aminoalkylen bearing pyridines. Suitable ureylene polymers have been disclosed in EP 2735627 A1 and EP 2922985 A1, said polyalkylenglycol bearing amino acids and peptides are published in EP 2113587 B9. EP3497267 discloses end-capped polyether compounds. EP 2537962 A1 teaches suitable aminoalkylene compounds bearing pyrrols and pyridines. WO 2016169952 A1 teaches suitable capped guanidine compounds. The total amount of leveller compounds in the acidic aqueous composition according to the present invention is preferably in the range of from 0.1 mg/L to 100 mg/L, based on the total volume of the composition. Own experiments have shown that such leveller compounds very often improve the process stability.

In a few cases, according to our own experiments, some leveller compounds as defined above slightly negatively (but still acceptably) affect the overpotential generated in the acidic aqueous compositions according to the invention. Thus, in a few cases it is preferred that the acidic aqueous composition according to the present invention (as defined above, preferably defined as being preferred) is substantially free of, preferably does not contain one or more than one leveller compound as defined above. In one embodiment of the acidic aqueous composition according to the present invention it is preferred, that the leveller is not polyethylenimine (PEI).

Preferably, the acidic aqueous composition according to the present invention contains at least one wetting agent. These wetting agents are also referred to as surfactants in the art. The at least one wetting agent is preferably selected from the group consisting of non-ionic, cationic and anionic surfactants. The total amount of wetting agents in the acidic aqueous composition according to the present invention is preferably in the range of from 0.01 to 5 wt.-%, based on the total weight of the acidic aqueous composition.

As mentioned above, the acidic aqueous composition according to the invention contains one or more than one suppressor (ii) consisting of or comprising one single N-heteroaromatic mono-ring, said mono-ring comprising at least two ring nitrogen atoms and more than one substituent covalently connected to one of said ring nitrogen atoms and/or a ring carbon atom, wherein said substituent independently is or comprises one or more than one linear or branched polyalkylene glycol moiety, and/or one or more than one linear or branched polyalkylene glycol block polyalkylene glycol or random polyalkylene glycol moiety.

Preferably, in the acidic aqueous composition according to the present invention the one or more than one linear or branched polyalkylene glycol moiety independently comprises a polyethylene glycol moiety and/or a polypropylene glycol moiety, wherein polypropylene can be based on n-propyl units or iso-propyl units, preferably a polyethylene glycol moiety.

An acidic aqueous composition is preferred according to the present invention, wherein the one or more than one linear or branched polyalkylene glycol block polyalkylene glycol moiety independently comprises a polyethylene glycol-block-polypropylene glycol moiety and/or a polypropylene glycol-block-polyethylene glycol moiety, preferably a polyethylene glycol-block-polypropylene glycol moiety or one or more than one linear or branched random polyalkylene glycol moiety independently comprises a random polyethylene glycol-polypropylene glycol moiety, wherein polypropylene can be based on n-propyl units or iso-propyl units.

Preferably, in the acidic aqueous composition according to the present invention the one or more than one suppressor (ii) comprises in total 1 to 4 aromatic ring carbon atoms, preferably 2 to 3, most preferred is 3.

Preferably, in the acidic aqueous composition according to the present invention the one single N-heteroaromatic mono-ring is a 6-membered ring or a 5-membered ring, preferably a 5-membered ring.

According to the present invention it is preferred that the one single N-heteroaromatic mono-ring does not comprise a ring oxygen atom. An acidic aqueous composition according to the present invention is preferred, wherein the one or more than one suppressor (ii) consists of carbon atoms, hydrogen atoms, nitrogen atoms, and oxygen atoms.

An acidic aqueous composition is preferred according to the present invention, wherein the one single N-heteroaromatic mono-ring is selected from the group consisting of a pyrazole ring, an imidazole ring, a 1,3,5-triazine ring, a 1,2,4-triazine ring, a 1,2,3-triazine ring, and a tetrazole ring preferably is selected from the group consisting of an imidazole ring and a 1,3,5-triazine ring, most preferably is an imidazole ring.

An acidic aqueous composition is preferred according to the present invention, wherein in the one or more than one suppressor (ii) one of said substituent is covalently connected to one of said at least two ring nitrogen atoms such that the nitrogen atom is positively charged.

Preferably, in the acidic aqueous composition according to the invention each of the one or more than one linear or branched polyalkylene glycol moiety and each of the one or more than one polyalkylene glycol block polyalkylene glycol or random polyalkylene glycol moiety, respectively, contains a terminal alkyl group, preferably a C1 to C4 alkyl group, most preferably a methyl group.

An acidic aqueous composition is preferred according to the present invention, wherein the one or more than one suppressor (ii) does not comprise an aromatic ring structure except the one single N-heteroaromatic mono-ring, preferably does not comprise any ring structure except the one single N-heteroaromatic mono-ring.

According to our own experiments, excellent results were obtained, if the one or more than one suppressor (ii) is selected from the group consisting of

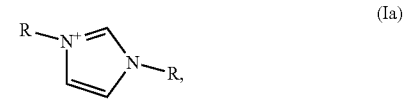

(Ia)

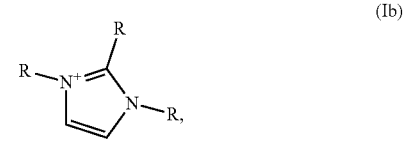

(Ib)

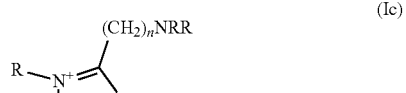

(Ic)

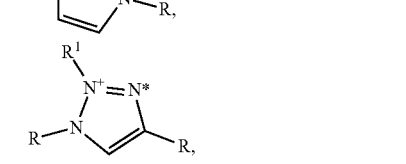

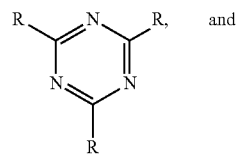

(Id)

and

-continued

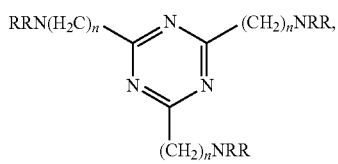
(Ie)

wherein each independently

R denotes a linear or branched polyalkylene glycol moiety, a linear or branched polyalkylene glycol block polyalkylene glycol moiety or random polyalkylene glycol (as defined above, preferably defined as being preferred) and $R^1$ is alkyl, preferably alkyl is methyl, ethyl or propyl, most preferably methyl, and n denotes 0, 1, 2, 3, 4, or 5, preferably 0, 1, 2, or 3.

The use of compounds (Ia), (Ib), (Ic), (Id), (Ie) and/or (If) as suppressor (ii) in acidic aqueous composition according to the present invention is therefore preferred. In particular, the use of (Ia), (Ib), (Ic), and/or (If), containing a positive charged nitrogen, is preferred.

An acidic aqueous composition according to the present invention is further preferred, wherein the one or more than one suppressor (ii) is selected from the group consisting of

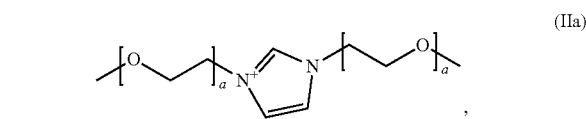
(IIa)

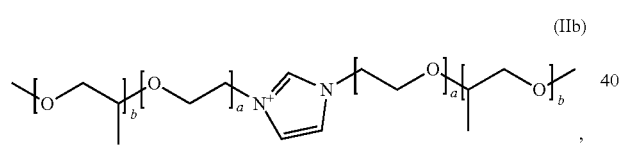
(IIb)

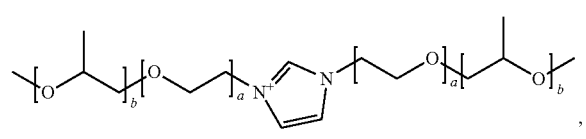
(IIb')

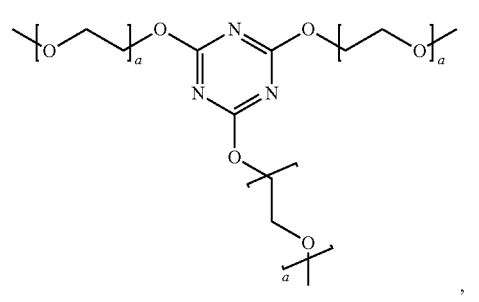
(IIc)

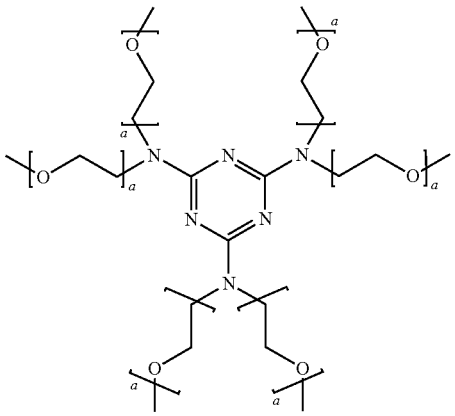
, and
(IId)

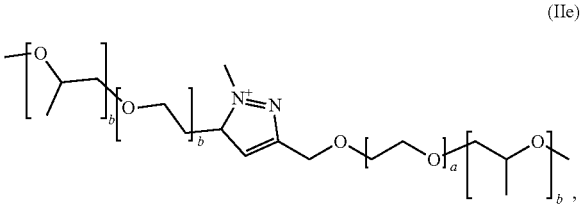
(IIe)

wherein each independently a denotes an integer in the range from 2 to 22, preferably in the range from 3 to 20, most preferably in the range from 4 to 16, and b denotes an integer in the range from 2 to 22, preferably in the range from 3 to 20, most preferably in the range from 4 to 16. Thus, a respective acidic aqueous composition for electrolytic copper plating according to the present invention (as defined above, preferably defined as being preferred) is in particular preferred. These are very preferred specific suppressors (ii) and, thus, result in very preferred compositions of the present invention comprising one or more than one suppressor (ii).

According to our own experiments, these compounds showed very good plating results and sufficiently high overpotentials compared to PEG. They are for an acidic aqueous composition for electrolytic metal plating, preferably for electrolytic copper plating, more preferably for a composition and method, respectively, as defined for the present invention.

Preferably, in the acidic aqueous composition according to the present invention the weight average molecular weight (Mw) of the suppressor (ii) is in the range of from 500 g/mol to 5,000 g/mol, preferably in the range of from 600 g/mol to 4,000 g/mol preferably in the range of from 700 g/mol to 3,000 g/mol, measured by gel permeation chromatography (GPC) using a calibration curve based on standard polystyrene.

The present invention also relates to the use of the acidic aqueous composition according to the present invention (as defined above, preferably defined as being preferred) for electrolytic copper plating, preferably for void-free copper filling of recessed structures (preferably recessed structures with an aspect ratio in the range from 1:20 to 20:1). Preferred recessed structures are trenches, blind micro vias, and through holes.

An acidic aqueous composition is preferred according to the present invention, wherein the at least one additional suppressor being different from the suppressor (ii), (suppressor (iii)) is a polymer comprising nitrogen and/or oxygen, preferably selected from the group consisting of polyvinylalcohol, carboxymethylcellulose, polyethylene glycol, polypropylene glycol, stearic acid polyglycolester, alkoxylated naphtholes, oleic acid polyglycolester, stearylalcohol-polyglycolether, nonylphenolpolyglycolether, octanolpolyalkylene glycolether, octanediol-bis-(polyalkylene glycolether), poly(ethylene glycol-ran-propylene glycol), poly(ethylene glycol)-block-poly(propylene glycol)-bock-poly(ethylene glycol), poly(propylene glycol)-block-poly(ethylene glycol)block-poly(propylene glycol, and poly(ethylene oxide)-poly(propylene oxide) (PEO-PPO) blocks bonded to a central ethylenediamine moiety also called as poloxamine.

The concentration of said optional additional suppressor (iii) preferably ranges from 0.0005 g/L to 1 g/L, more preferably from 0.001 g/L to 0.5 g/L.

The above-mentioned features regarding the acidic aqueous composition according to the present invention (preferably features defined as being preferred) do also apply to the use of the acidic aqueous composition for electrolytic copper plating and void-free copper filling.

The present invention relates also to the use a suppressor (ii) as defined in the text above in an acidic aqueous composition for electrolytic metal plating, preferably in an acidic aqueous composition for electrolytic copper plating, preferably in an acidic aqueous composition for electrolytic copper plating according to the present invention (as defined above, preferably defined as being preferred).

The above-mentioned features regarding the acidic aqueous composition (as defined above, preferably defined as being preferred), do also apply to the aforementioned use of the acidic aqueous composition for electrolytic copper plating and to the aforementioned use of the compound.

The present invention relates furthermore to a suppressor for electrolytically depositing a copper deposit comprising, preferably consisting of,
one single N-heteroaromatic mono-ring, said mono-ring comprising at least two ring nitrogen atoms and more than one substituent covalently connected to one of said ring nitrogen atoms and/or a ring carbon atom, wherein said substituent independently is or comprises
one or more than one linear or branched polyalkylene glycol moiety, and/or
one or more than one linear or branched polyalkylene glycol block polyalkylene glycol or random polyalkylene glycol moiety,
with the proviso that
if said suppressor comprises a OH group, then it is a terminal OH group of said polyalkylene glycol moiety and polyalkylene glycol block polyalkylene glycol or random polyalkylene glycol moiety, respectively,
said compound does not comprise $NH_2$ groups, halide atoms and sulfur atoms.

A suppressor according to the present invention is preferred, wherein the suppressor is selected from the group consisting of

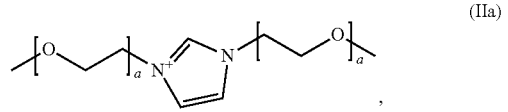
(IIa)

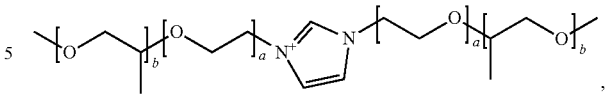
(IIb)

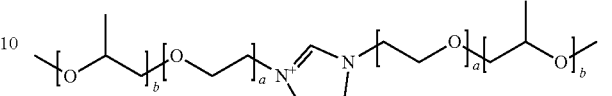
(IIb')

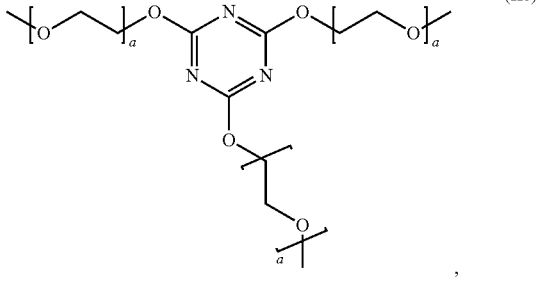
(IIc)

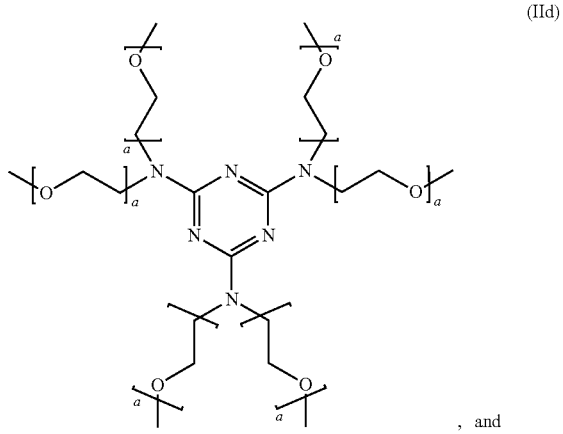
(IId)

, and

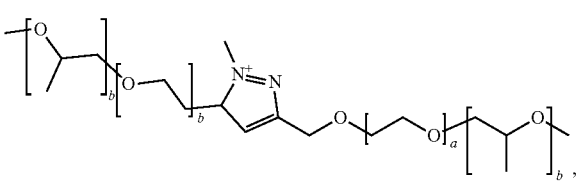
(IIe)

wherein each independently
a denotes an integer in the range from 2 to 22, preferably in the range from 3 to 20, most preferably in the range from 4 to 16, and
b denotes an integer in the range from 2 to 22, preferably in the range from 3 to 20, most preferably in the range from 4 to 16,
preferably the suppressor is a compound of formulae (IIb), (IIb'), (IId), or (IIe), even more preferably the suppressor is a compound of formulae (IIb), (IIb') or (IIe).

In one embodiment of the present invention it is preferred, wherein the one or more than one linear or branched polyalkylene glycol moiety is not a polyethylene glycol moiety if the one single N-heteroaromatic mono-ring is an imidazole ring, preferably if the one or more than one linear or branched polyalkylene glycol moiety is not a polyethylene glycol moiety.

The above-mentioned features regarding the suppressor (ii) contained in the aqueous composition for electrolytic copper plating according to the present invention (as defined above, preferably defined as being preferred), do also apply to the aforementioned suppressor according to the present invention.

The use of compounds (IIa), (IIb), (IIb'), (Ic), (Id), (Ie) and/or (If) as suppressor (ii) in acidic aqueous composition for copper plating according to the present invention is preferred, even more preferred is the use of the suppressors (IIb), (IIb'), (IId) and (IIe), most preferred (IIb), (IIb'), or (IIe).

The present invention relates furthermore to a method of electrolytic copper plating, comprising the steps
(a) providing or manufacturing a substrate suitable for electrolytic copper plating, preferably a substrate with a structured layer on its surface,
(b) contacting the substrate obtained in step (a), or obtained in an additional step after step (a) but before step (b), with the acidic aqueous composition according to the present invention (as defined above, preferably defined as being preferred)
and applying an electrical current such that the copper is electrolytically plated (deposited) onto the substrate as a copper deposit.

In the method according to the present invention the substrate and at least one anode are connected to a current or respective voltage source. Upon applying a current, copper is plated (deposited) onto said substrate (at least on parts of the substrate's surface). In some cases, step (b) is carried out directly after step (a). In other cases, it is preferred that after step (a) a cleaning and/or rinsing step is included as an additional step. In such a case a cleansed/rinsed substrate is obtained. Preferably, such a cleansed/rinsed substrate is directly contacted as defined in step (b).

Preferably, the substrate is selected from the group consisting of printed circuit boards, IC substrates, semiconducting wafers, ceramics, and glass substrates. Preferred are substrates of the aforementioned group which have recessed structures such as trenches, blind micro vias, through silicon vias, through holes and through glass vias. Therefore, a substrate is preferred comprising one or more than one recessed structure selected from the group consisting of trenches, blind micro vias, and through holes. In the method of the present invention preferably these structures are void-free filled with copper (see "Examples" below). Thus, preferred is a method of the present invention, wherein in step (b) an electrical current is applied such that copper is electrolytically plated onto the substrate and recessed structures, preferably trenches, blind micro vias, and through holes are void-free filled with copper. The method can also be used for a substrate which was treated with a dual damascene process.

In many cases it is preferred that the substrate contains a metal seed layer, more preferably a copper seed layer. In some cases, the substrate preferably comprises a resin, ceramics, glass, or silicon, more preferably with a metal seed layer, even more preferably with a copper seed layer.

During the method of electrolytic copper plating according to the present invention, the acidic aqueous composition according to the present invention is preferably agitated, more preferably by a strong inflow and, where applicable, by clean air being blown in, such that the surface of the composition undergoes strong movement. This means that the substance transport is maximized in the vicinity of the cathodes and anodes so that a greater current density is made possible. Movement of the cathodes also improves the substance transport at the respective surfaces. In addition, convection can also be produced in the composition by rotating the substrate. Constant diffusion-controlled deposition is achieved by means of the increased convection and electrode movement. The substrate can be moved in a horizontal and vertical manner and/or by means of vibration. A combination with the air blown into the composition is particularly effective, and, thus preferred.

In the method of electrolytic copper plating according to the present invention (as described above, preferably described as being preferred) step (b) is preferably carried out at a temperature in the range of from 15° C. to 50° C., more preferably at a temperature in the range of from 15° C. to 40° C. This means that in step (b) the composition of the present invention has a temperature as defined above.

Preferably, a cathodic current density (average density) in the range of from 0.05 A/dm$^2$ to 12 A/dm$^2$ is applied, more preferably in the range of from 0.1 A/dm$^2$ to 7 A/dm$^2$, even more preferably in the range of from 0.1 A/dm$^2$ to 3 A/dm$^2$. However, current densities exceeding the above-mentioned ranges are not excluded, in particular for pulse plating methods.

Preferably, step (b) in the method of electrolytic copper plating according to the present invention (as described above, preferably described as being preferred) is carried out in DC plating mode (DC plating method), pulse plating mode including reverse pulse plating mode (pulse plating method and reverse pulse plating method, respectively) or in combinations thereof.

Pulse plating typically includes unipolar pulsed currents, wherein the depositing current is regularly interrupted by current pauses. Reverse pulse plating typically includes pulses of reversed currents during the plating process.

The reverse pulse plating method was developed for the electrolytic deposition in particular of copper on circuit boards with a high aspect ratio and is described, for example, in DE 42 25 961 C2 and DE 27 39 427 A 1. Where higher current densities are used, improved surface distribution and throwing power is achieved in the through holes.

In the method of the present invention (as defined above, preferably defined as being preferred), inert (insoluble) or soluble anodes are used. In some cases, inert anodes are preferred. Insoluble anodes are inert during the plating process and consequently do not change their shape. This enables a time constant geometry during the plating process. In particular precious metals, such as platinum or also so-called valve metals such as titanium, coated with mixed oxides of precious metals, for example with a coating of ruthenium oxide and iridium oxide, are preferably used as insoluble anodes in the method according to the present invention. In some cases, it is preferred that the insoluble anodes are in the form of expanded metal. In order to obtain a supplement of copper ions when using insoluble anodes, a copper compound needs to be dissolved in the acidic aqueous composition according to the present invention (for copper sources see the text above), or metallic copper is brought into contact with the composition. Metallic copper dissolves under the influence of oxygen dissolved in the composition or with the help of compounds that form the oxidised form of a redox system, for example with the help of Fe (III) ions dissolved in the composition which are thereby reduced to Fe (II) ions. The Fe (II) ions are oxidised at the insoluble anode back to Fe (III) ions. The Fe (II)/Fe (III) ions can originate, for example, from a corresponding iron sulfate salt. The concentration of Fe (II) ions in the composition is preferably 8 to 12 g/L and that of Fe (III) ions preferably 1 to 5 g/L, based on the total volume of the composition.

However, in other cases soluble copper anodes are preferred. The copper consumed during the deposition (plating) process is typically supplemented electrochemically via soluble copper anodes. Soluble copper anodes with a content of 0.02 to 0.067 percent by weight phosphorus are in particular preferred.

In the method according to the present invention, copper is preferably plated both in the conventional manner, by immersing the substrate into the composition that is located in an immersion bath container and polarizing the substrate in relation to an anode that is located in the same composition, and also by a horizontal plating method. The latter plating method is carried out in a conventional horizontal apparatus, through which the substrates are conveyed in a horizontal position and direction of transport, at the same time being brought into contact with the acidic aqueous composition. The anodes are also disposed in a horizontal position in the apparatus along the transport path for the substrates. These types of apparatus are disclosed, for example, in DE 36 24 481 A1 and DE 32 36 545 A1. In addition, semiconductor wafers are preferably treated in so-called cup-platers, in which a respective wafer is disposed in the horizontal position above an anode that is also disposed in a horizontal position. The cup-plater is filled with the acidic aqueous composition according to the present invention. Consequently, both the wafer and the anode are in contact with the composition. Preferably, the wafer rotates during the depositing process.

Furthermore, the above-mentioned features regarding the acidic aqueous composition (as defined above, preferably defined as being preferred), preferably do apply to the method of electrolytic copper plating according to the present invention.

A method according to the present invention is preferred, wherein the plated copper deposit forms a plurality of copper pillars and/or a plurality of copper conducting traces, preferably wherein the copper deposit is a plurality of cupper conducting traces, more preferably wherein the copper deposit is a plurality of cupper conducting traces in an redistribution layer. The plurality of copper pillars is preferably plated by so-called bottom-up plating of the recessed structures. The plurality of copper conducting traces as through holes is preferably plated/filled by so-called x-plating, wherein the through hole is first plated in the middle of the through hole, closing the hole by generating to blind vias and then filling the generated blind vias.

A method according to the present invention is preferred, wherein the copper deposit deposited in step (b) has an aspect ratio in the range from 1:20 to 20:1.

A method according to the present invention is preferred, wherein the copper deposit deposited in step (b) has a height in the range from 0.2 µm to 200 µm.

A method according to the present invention is preferred, wherein the copper deposit deposited in step (b) has a width in the range from 0.2 µm to 200 µm.

A method according to the present invention is preferred, wherein in step (b) direct current is applied, preferably direct current with a current density in the range from 0.1 ASD to 120 ASD, most preferably in step (b) only direct current is applied, preferably only direct current with a current density in the range from 0.2 ASD to 80 ASD.

A method according to the present invention is preferred, wherein in step (b) direct current is applied, preferably direct current with a current density in the range from 0.1 ASD to 4 ASD.

A method according to the present invention is preferred, wherein in step (b) direct current is applied, preferably direct current with a current density in the range from 1 ASD to 10 ASD.

A method according to the present invention is preferred, wherein in step (b) direct current is applied, preferably direct current with a current density in the range from 10 ASD to 80 ASD.

The following examples illustrate the benefits of the present invention.

EXAMPLES

A. Synthesis

A1. Synthesis of a Compound of Formula (IIb)

In a first step polyethylene glycol (PEG, Alfa Aesar, Mw=202 g/mol) was reacted by means of nucleophilic substitution with para-toluenesulfonyl chloride (p-TsCl, Merck, 98%) in tetrahydrofuran (THF, VWR, 100%)/water, and the presence of NaOH, at 0° C. for 20 hours into tosylated polyethylene glycol ((bis-Ts)-PEG, yield: appr. 70%), which was further purified in a subsequent step.

In a second step, the (bis-Ts)-PEG was reacted by means of nucleophilic substitution with polypropylene glycol monomethylether (PPG206, M=206 g/mol, three monomeric units) in THF and in the presence of potassium tert-butoxide (KO-t-butyl, Merck, 98%), at 50° C. for 20 hours into tosylated polyethylene glycol-block-polypropylene glycol methylester (block intermediate, yield: appr. 15%).

In a third step, the block intermediate was reacted by means of nucleophilic substitution with imidazole (Merck, 100%) in THF and in the presence of KO-t-butyl at 65° C. for 165 hours into a compound of formula (IIb) (yield: appr. 25%, Mw=797). In a subsequent step, the compound was further purified by HPLC (ACN/$H_2O$: 30/70 vol-%; yield: appr. 10%).

A2. Synthesis of a Compound of Formula (IIc)

In a first step polyethylene glycol monomethylether (PEGMe, Alfa Aesar, Mw=350 g/mol) was reacted with trichlorotriazine (Acros Organics, 99%) in THF and in the presence of KO-t-butyl at a temperature in the range from 0° C. to 60° C. for 20 hours into a compound of formula (IIc) (yield: appr. 23%, Mw=963 g/mol). In a different approach PEGMe with Mw=750 g/mol was utilized instead of PEGMe with Mw=350 g/mol. As a result, a compound of formula (IIc) with Mw=2152 g/mol was obtained.

B. Depositing Results

B1. Example 1: Acidic Aqueous Composition (According to the Invention)

In a first step a plating bath was prepared by mixing (i) copper ions (added as copper (II) sulfate pentahydrate, $CuSO_4 * 5\ H_2O$ (also used in the following examples)) in a total amount of 60 g/L, (ii) compound of formula (IIb) in a total amount of 0.010 g/L, (iii) sulfuric acid in a total amount of 50 g/L, (iv) chloride ions (added as HCl) in a total amount of 0.030 g/L, (v) a disulfide as accelerator (Spherolyte® Acc 10) in a total amount of 3 mL/L, and (vi) deionized water.

In a second step electrolytic copper plating was carried out utilizing the acidic composition prepared in the first step. The temperature of the plating bath was 25° C. and a current density of 2 mA/cm² was applied for 50 minutes. A copper layer was electroplated onto a wafer substrate provided with a copper seed layer and a feature diameter of 10 µm with aspect ratios of approximately 6:1.

The vias are completely filled without defects as voids. Filling height is 68.2 µm. A photograph of a cross section of the copper metallized wafer substrate is shown in FIG. 1.

B.2. Example 2: Acidic Aqueous Composition (Comparative Example, Not According to the Invention)

Example 1 was repeated, but in the acidic aqueous comparison composition according to Example 2 (not according to the invention) Tetronic® 304 (poly(ethylene oxide)-poly(propylene oxide) (PEO-PPO) blocks bonded to a central ethylenediamine moiety) was used instead of a compound of of formula (IIb). Tetronic® 304 is a common additive in respective compositions, is commercially available and described in more detail in paragraph [0027] of the international patent application WO 2008157612 A1.

In a first step the comparison composition was prepared by mixing (i) copper ions in a total amount of 60 g/L, (ii) Tetronic® 304 in a total amount of 0.01 g/L, (iii) sulfuric acid in a total amount of 50 g/L, (iv) chloride ions (added as HCl) in a total amount of 0.030 g/L, (v) a disulfide as accelerator (Spherolyte® Acc 10) in a total amount of 3 mL/L, and (vi) deionized water.

In a second step electrolytic copper plating was carried out utilizing the acidic composition prepared in the first step. The temperature of the plating bath was 25° C. and a current density of 2 mA/cm² was applied for 50 minutes. A copper layer was electroplated onto a wafer substrate provided with a copper seed layer and a feature diameter of 10 µm with aspect ratios of approximately 6:1.

Figure 2:
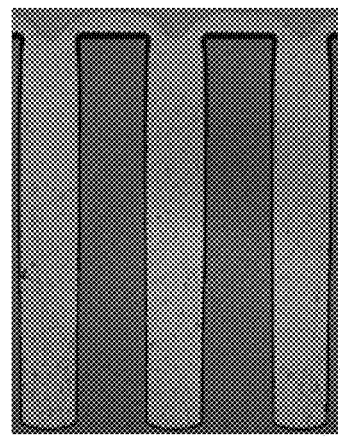
FIG. 2 is a photograph of a cross section of the copper metallized wafer substrate obtained by Example 2 as an embodiment of the present invention.

The vias are incompletely filled (dimple) without defects as voids. Filling height is 60 µm. A photograph of a cross section of the copper metallized wafer substrate is shown in FIG. 2.

The invention claimed is:

1. An acidic aqueous composition for electrolytically depositing a copper deposit, the composition comprising
   (i) copper (II) ions,
   (ii) one or more than one suppressor comprising one single N-heteroaromatic mono-ring, said mono-ring comprising at least two ring nitrogen atoms and more than one substituent covalently connected to one of said ring nitrogen atoms and/or a ring carbon atom, wherein said substituent independently is or comprises
      one or more than one linear or branched polyalkylene glycol moiety, and/or
      one or more than one linear or branched polyalkylene glycol block polyalkylene glycol or random polyalkylene glycol moiety,
      with the proviso that
         if said suppressor comprises a OH group, then it is a terminal OH group of said polyalkylene glycol moiety, polyalkylene glycol block polyalkylene glycol or random polyalkylene glycol moiety, respectively, and said suppressor does not comprise NH₂ groups, halogen atoms, and sulfur atoms,
wherein the one or more than one suppressor of (ii) is selected from the group consisting of

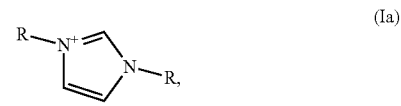

(Ia)

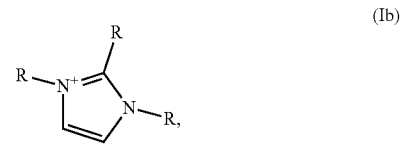

(Ib)

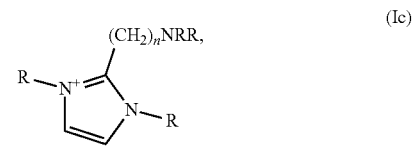

(Ic)

(If)

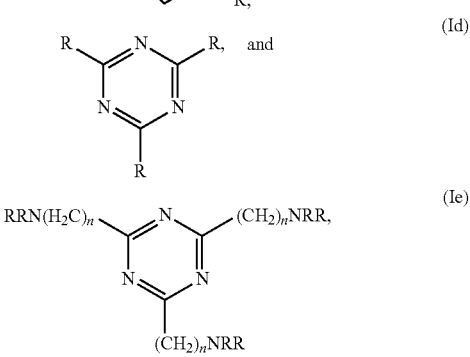

(Id)

(Ie)

wherein each independently
   R denotes a linear or branched polyalkylene glycol moiety or a linear or branched polyalkylene glycol block polyalkylene glycol or a random polyalkylene glycol moiety and R¹ is alkyl, and
   N denotes 0, 1, 2, 3, 4, or 5.

2. The composition of claim 1 further comprising
   (iii) at least one additional suppressor being different from the suppressor (ii), and
   (iv) at least one accelerator being different from the suppressors (ii) and (iii).

3. The composition of claim 2, wherein the at least one additional suppressor being different from the suppressor (ii) is a polymer comprising nitrogen and/or oxygen atoms.

4. The composition of claim 1, wherein the one or more than one suppressor of (ii) is selected from the group consisting of

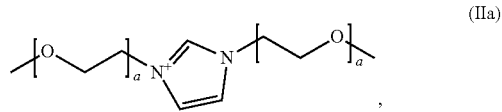

(IIa)

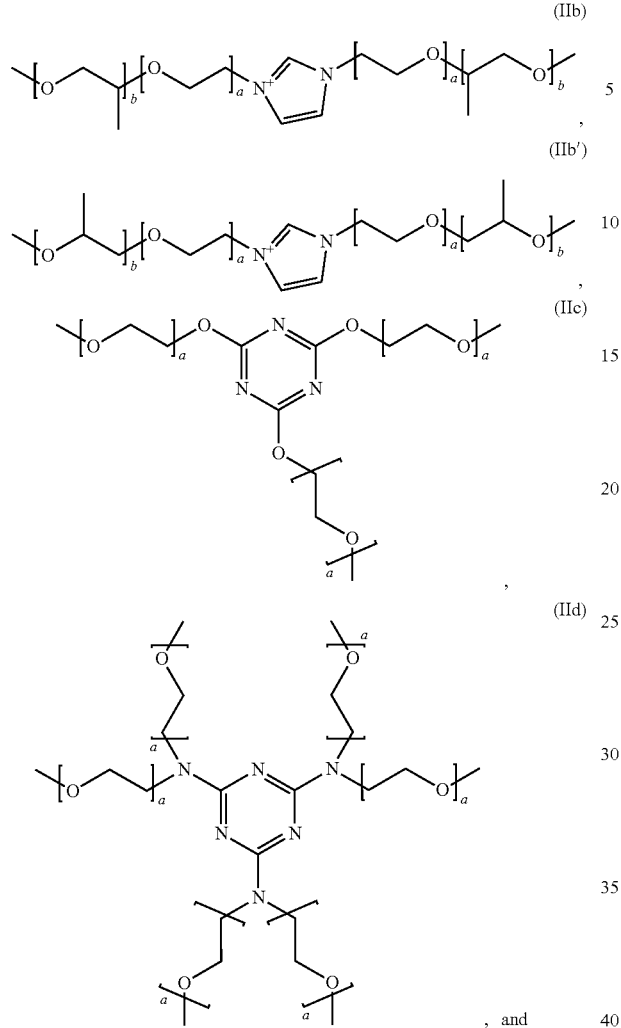

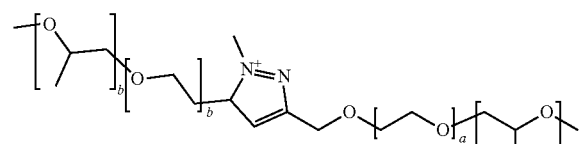

wherein each independently a denotes an integer in the range from 2 to 22, and b denotes an integer in the range from 2 to 22.

5. The composition of claim 1, wherein the suppressor of (ii) has a weight average molecular weight (Mw) in the range from 500 g/mol to 5000 g/mol.

6. The composition of claim 1, wherein the one or more than one suppressor of (ii) is present in a total amount in the range from 10 mg/L to 1000 mg/L, based on the total volume of the acidic aqueous composition.

7. Method of electrolytic copper plating, comprising the steps:

(a) providing or manufacturing a substrate suitable for electrolytic copper plating, (b) contacting the substrate obtained after step (a), or obtained after an additional step after step (a) but before step (b), with the acidic aqueous composition according to claim 1 and applying an electrical current such that the copper is electrolytically plated onto the substrate as a copper deposit.

8. The method of claim 7, wherein the copper deposit forms a plurality of copper pillars and/or a plurality of copper conducting traces.

9. The method of claim 7, wherein the substrate comprises one or more than one recessed structure selected from the group consisting of trenches, blind micro vias, and through holes.

* * * * *